(12) United States Patent
Bashkin et al.

(10) Patent No.: US 6,258,941 B1
(45) Date of Patent: Jul. 10, 2001

(54) RNA HYDROLYSIS

(75) Inventors: James K. Bashkin; Michael K. Stern, both of University City; Anil S. Modak, Maryland Heights, all of MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 07/947,071

(22) Filed: Sep. 16, 1992

Related U.S. Application Data

(63) Continuation of application No. 07/550,001, filed on Jun. 14, 1990, now abandoned.

(51) Int. Cl.$^7$ .................................................. C07H 21/00
(52) U.S. Cl. ........................ 536/22.1; 546/82; 546/259; 546/257; 536/25.3
(58) Field of Search ...................... 546/82, 259, 257; 532/27, 25.3; 536/22.1, 25.3

(56) References Cited

U.S. PATENT DOCUMENTS

| | | | | |
|---|---|---|---|---|
| 4,267,335 | * | 5/1981 | McGill | 546/257 |
| 4,711,955 | * | 12/1987 | Ward | 536/27 |
| 4,795,700 | | 1/1989 | Dervan et al. | 435/5 |
| 4,837,312 | | 6/1989 | Dervan et al. | 536/27 |
| 4,859,777 | * | 8/1989 | Toner | 546/257 |
| 4,873,333 | * | 10/1989 | Stapersma | 546/257 |
| 4,933,455 | * | 6/1990 | Stapersma | 546/257 |

FOREIGN PATENT DOCUMENTS

| | | | |
|---|---|---|---|
| WO 88/04300 | | 6/1988 | (WO) . |
| WO 89/05853 | | 6/1989 | (WO) . |
| 0003381 | * | 4/1990 | (WO) ................ 536/25.3 |

OTHER PUBLICATIONS

Cornelius, R. D., Inorg. Chem., 1980, 19, pp. 1286–1290.
Norman, P. R. et al, J. Am. Chem. Soc., 1982, 104, pp. 2356–2361.
Tafesse, F., Inorg. Chem., 1985, 24, 2593–2594.
Chin, J. et al, Can. J. Chem., 1987, 65, 1882–1884.
Chin, J. et al, J. Am. Chem. Soc., 1989, 111, pp. 4103–4105.
Eichhorn, G., et al, Biochemistry, 1971, 10, pp. 2014–2017.
Butzow, J. J., et al, Nature, 1975, 254, pp. 358–359.
Breslow, R., et al, Proc. Natl. Acad. Sci., 1989, 86, pp. 1746–1750.
Stein, C. A., et al, Cancer Research, May, 1988, 48, pp. 2659–2668.
Chen, C. B., et al, J. Am. Chem. Soc., 1988, 110, pp. 6570–6572.
Zuckerman, R. N., et al, J. Am. Chem. Soc., 1988, 110, pp. 6592–6594.
Zuckerman, R. N., et al, Proc. Natl. Acad. Sci.USA, 1989, 86, pp. 1766–1770.
Corey, D. R., et al, Biochemistry, 1989, 28, pp. 8277–8286.
Zuckerman, R. N., et al, J. Am. Chem. Soc., 1988, 110, 1614–1615.
Chen et al. Proc. Natl. Acad. Sci 83: 7147–7151 (1986).*

* cited by examiner

*Primary Examiner*—Irene Marx
(74) *Attorney, Agent, or Firm*—Howell & Haferkamp, L.C.

(57) ABSTRACT

The selected sequence-directed hydrolysis of RNA under physiologically relevant conditions is described using conjugates comprising metal complexes covalently linked to oligodeoxynucleotides as hydrolysis agents. The oligodeoxynucleotide portions of the agents are selected to provide molecular recognition via the Watson Crick base pairing to the target RNA sequence to be hydrolyzed. A method is described for determining the RNA hydrolysis effectiveness of metals and ligands used to form the metal complexes useful in this invention.

14 Claims, 11 Drawing Sheets

| Compound Structure | Chemical name |
|---|---|
| 11 | 5'-[4-[4'-Methyl(2,2'-bipyridin)-4-yl]butyl-phosphate] 2'-deoxy-thymidine triethylammonium salt |
| 16 | 5-[3-[[2-[[4-[4'-Methyl(2,2'-bipyridin)-4-yl] -1-oxobutyl]amino]ethyl]amino] -3-oxopropyl]-2'-deoxyuridine |

FIG. 8B

| Compound Structure | Chemical name |
|---|---|
|  26 | 5-[[2-[[2-Amino-3-(1H-imidazol-4-yl)-1-oxopropyl]amino]ethyl]thio]-2'-deoxy-uridine |
|  27 | 5-[3-[[2-[[(2,6-Diamino)-1-oxohexyl]amino]ethyl]amino]-3-oxopropyl]-2'-deoxy-uridine dihydrochloride |

RNA HYDROLYSIS

This is a Continuation of application Ser. No. 07/550,001, filed on Jun. 14, 1990, now abandoned.

FIELD OF INVENTION

This invention relates to sequence-directed RNA hydrolysis under physiologically relevant conditions and particularly to metal complexes covalently linked to oligodeoxynucleotides as sequence-directed RNA hydrolysis agents.

BACKGROUND OF THE INVENTION

Recently hydrolysis of phosphate esters has received extensive investigation as reported in the art due to the relevance of this chemistry to biological systems, and specifically transition metal complexes have been examined as phosphate ester hydrolysis catalysts in order to model the reactions catalyzed by the ATPase and phosphatase classes of enzymes. Such reported studies have generally employed activated p-nitrophenyl phosphate esters or phosphate anhydrides (ATP) as substrates (R. D. Cornelius, *Inorg. Chem.* 1980, 19, 1286–1290; P. R. Norman et al, *J. Am. Chem. Soc.* 1982, 104, 2356–2361 and F. Tafesse et al, *Inorg. Chem.* 1985, 24, 2593–2594). It has been reported that tetramine complexes of Co(III) are capable of promoting the hydrolysis of adenosine 3',5'-monophosphate (cAMP) (J. Chin et al, *Can. J. Chem.* 1987, 65, 1882–1884) and adenosine monophosphate (AMP) (J. Chin et al, *J. Am. Chem. Soc.* 1989, 111, 4103–4105). Also, it is known that many divalent cations are capable of catalyzing the hydrolysis of RNA (J. J. Butzow et al, *Biochemistry* 1971, 10, 2016–2027 and J. J. Butzow et al, *Nature* 1975, 254, 358–359). Additionally, zinc ion in the presence of imidazole buffers has been shown to catalyze the hydrolysis of the RNA dimer 3',5'-UpU at 80° C. (R. Breslow et al, *Proc. Natl. Acad. Sci.* 1989, 86, 1746–1750).

C. A. Stein et al, *Cancer Research* May, 1988, 48, 2659–2668 gives a detailed review on the application of antisense oligodeoxynucleotides as modulators of gene expression and concludes by proposing a more subtle and effective approach would be to attach a chemical group to the oligomer that can result in localized catalytic hydrolysis of RNA. This technique would be more specific than the use of a radical-producing group such as iron EDTA. Stein et al theorizes that a suitable RNA hydrolysis group would be an imidazole group, which is known to be involved in phosphodiester hydrolysis in the active site of ribonuclease enzymes.

University Patents, Inc. in PCT International Patent Application published under number WO 88/04300 on Jun. 16, 1988 discloses RNA enzymes or ribozymes, acting as endoribonucleases, as catalyzing the cleavage of RNA molecules with a sequence specificity of cleavage greater than that of known ribonucleases and approaching that of the DNA restriction endonucleases, thus serving as RNA sequence-specific endoribonucleases. Ribozymes are entirely or partly comprised of RNA itself, and therefore are chemically and enzymatically highly unstable relative to Applicants' DNA-based compounds. Such instability detracts from the practical applicability of RNA hydrolysis agents.

C. B. Chen et al, *J. Am. Chem. Soc.* 1988, 110, 6570–6572 describes that 1,10-phenanthroline-copper(II) is effective for targeted cleavage of both RNA and DNA and thus is useful for sequence-specific cleavage of RNA. This teaching is directed to oxidative cleavage of RNA by metal complexes linked to DNA at a temperature of 65° C. as opposed to the hydrolytic cleavage of RNA under physiologically relevant conditions required by Applicants' invention. The ancillary reagents, in the quantities required to drive the Chen et al oxidative degradation of RNA, are not compatible with living cells; furthermore, the 1,10-phenanthrolinecopper-oligodeoxynucleotide conjugate employed is itself degraded oxidatively under the conditions of oxidative RNA cleavage (the rate of oxidative cleavage by the 1,10-phenanthrolinecopper system is similar for both RNA and DNA).

P. G. Schultz and coworkers in a series of articles (D. R. Corey et al, *J. Am. Chem. Soc.* 1988, 110, 1614–1615; R. Zuckerman et al, *J. Am. Chem. Soc.* 1988, 110, 6592–6594 and R. Zuckerman et al, *Proc. Natl. Acad. Sci. USA* 1989, 86, 1766–1770) have described the preparation of site-selective DNA and RNA hydrolysis agents comprised of an enzyme (staphylococcal nuclease, ribonuclease S, or mutants of these parent enzymes) covalently linked to oligodeoxynucleotides. In one report (D. R. Corey et al, *Biochemistry* 1989, 28, 8277–8286), the location of the linker arm and its length were varied, which resulted in changes in catalytic efficiency and site of cleavage.

Considerable art has been developed on cleavage of RNA utilizing enzymes and ribozymes. At present the art is void of a teaching using metal complexes which cleave RNA hydrolytically at a physiologically relevant pH and temperature as synthetic analogs for enzymes or ribozymes to obtain sequence-directed hydrolysis of RNA. Sequence-directed RNA hydrolysis is highly desirable today in order to prepare catalytic antisense oligodeoxynucleotides useful as a means for inhibiting the expression of specific genes. Such RNA hydrolysis is necessary to provide a basis for catalytic antisense drug development.

STATEMENT OF THE INVENTION

This invention is directed to the hydrolytic cleavage of RNA at physiologically relevant conditions. The underlying basis of this invention is the use of metal complexes which perform as synthetic analogs for enzymes or ribozymes in the hydrolysis of RNA. Conjugate as used herein means a compound comprised of a metal complex covalently linked to a nucleoside or nucleotide. Oligodeoxynucleotide conjugate as used herein means a compound comprised of a metal complex covalently linked to an oligodeoxynucleotide.

A first aspect of this invention is directed to the discovery of metal complexes useful for promoting RNA hydrolysis. A second aspect of this invention is directed to a conjugate which is active for RNA hydrolysis comprised of a metal complex covalently linked to a nucleoside or nucleotide. A third aspect of this invention is directed to the sequence-directed hydrolytic cleavage of RNA by a metal complex covalently linked to an oligodeoxynucleotide. The oligodeoxynucleotide provides molecular recognition via Watson Crick base pairing to the target RNA sequence.

Accordingly, a major object of this invention is to provide for the hydrolysis of RNA at physiologically relevant conditions. Other objects of this invention include (1) the discovery of metal complexes which are effective for the hydrolysis of RNA, (2) the preparation of conjugates which retain RNA cleavage behavior, (3) the preparation of oligodeoxynucleotide conjugates effective for the sequence-directed hydrolysis of RNA under physiologically relevant conditions. Other objects and advantages of this invention will become apparent upon further study of this disclosure and the appended claims.

DESCRIPTION OF THE DRAWINGS

The structures of the compounds identified below by bold numbers in parenthesis are shown in reaction "Schemes" 1–6.

SUMMARY OF THE INVENTION

Figure 1A:
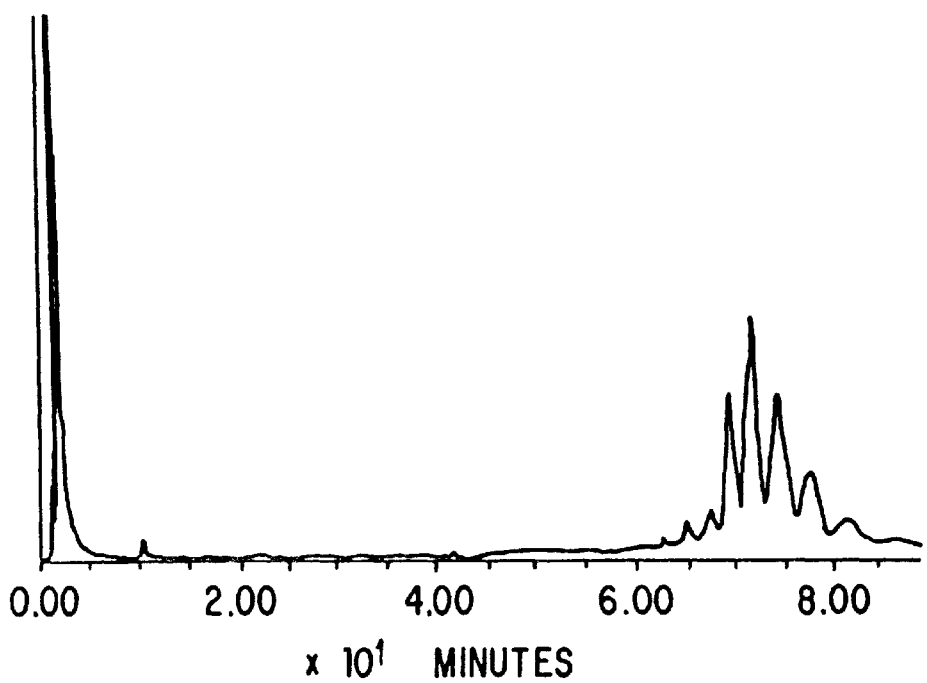
In FIG. 1 there is shown a typical example of Applicants' HPLC assay of the hydrolysis of RNA [poly(A)$_{12-18}$] by the metal complex, Zn—N—Me(CR). A, Time=0 hours; B, Time=18 hours.

The reaction schemes 1–6 show by compound formulas the synthetic paths used in Applicants' Examples.

Scheme 1 depicts the synthesis of compound (5) as described in Applicants' Example III.

Scheme 2 depicts the synthesis of compound (11) as described in Applicants' Example VI.

Scheme 3 depicts the synthesis of compound (16) as described in Applicants' Example IX.

Scheme 4 depicts the synthesis of compounds (20) and (23) as described in Applicants' Example XII.

Scheme 5 depicts the synthesis of compound (30) as described in Applicants' Example XIV.

Scheme 6 depicts the sequence-directed cleavage of tRNA$^{Tyr}$ by compound (32) as described in Applicants' Example XV.

The hydrolytically effective oligodeoxynucleotide conjugates of this invention are comprised of a desired organic molecule, herein referred to as the ligand, a metal ion, which imparts the hydrolytic activity, and a desired oligodeoxynucleotide.

Applicants' invention is based on metal complexes which are effective for RNA hydrolysis, and the preparation of such metal complexes covalently linked to nucleosides, nucleotides and oligodeoxynucleotides. The metal complexes covalently linked to the nucleosides, nucleotides and oligodeoxynucleotides distinguishes Applicants' invention from the speculation of the C. A. Stein et al and the teaching of the P. G. Schultz et al references described above. Certain compounds of the type proposed by Stein et al, comprised of imidazole attached to nucleosides and oligodeoxynucleotides, were prepared and found not to be effective for RNA hydrolysis under the criteria of Applicants' invention. Such compounds and their lack of RNA hydrolysis activity are shown below in Table II as compounds (24), (25) and (26).

Agents as used herein means Applicants' synthetic RNA hydrolysis compounds comprising a metal and a ligand, or metal complex, covalently linked to an oligodeoxynucleotide. The oligodeoxynucleotide provides sequence-directed recognition of RNA targets under physiologically relevant conditions. The agents of this invention are effectively artificial enzymes which mimic natural ribonucleases and ribozymes. These agents possess several advantages over ribonucleases and ribozymes in applications where sequence-directed RNA hydrolysis is desired. Such advantages include (1) enhanced specificity over ribonucleases, (2) increased chemical stability over ribozymes, (3) ease of production and isolation by standard chemical techniques, (4) the ability to design sequence specificity towards any targeted RNA strand, (5) low molecular weight, (6) drug delivery and (7) ability to control hydrolytic activity by altering the nature of the metal complex. These are important aspects of Applicants' invention which permits the practical application of sequence-directed RNA hydrolysis. These aspects of Applicarts' invention provide considerable novelty and advantages over the prior art teachings, such as the University Patents, Inc. PCT Patent Application and the P. G. Schultz et al and C. B. Chen et al references, described above.

The nucleic acid hydrolysis compounds of Schultz et al differ from Applicants' invention in several import aspects. The nucleic acid cleavage behavior taught by Schultz et al is provided by an enzyme, not the synthetic small molecule hydrolysis agents (artificial enzymes) used by Applicants. The enzymes are subject to proteolytic degradation by other enzymes. Staphylococcal nuclease is dependent on added calcium for its activity. Ribonuclease S is a noncovalent complex comprised of the S-protein and S-peptide derived from ribonuclease A. This complex is subject to dissociation, which results in loss of cleavage efficiency and specificity. Oligodeoxynucleotide-staphylococcal nuclease conjugates were shown to cleave DNA as well as RNA; thus, they lack the specificity of Applicants' agents for RNA hydrolysis alone. This high activity limits the specificity of the enzyme-based systems developed by Schultz et al because nonspecific cleavage events are common. The specificity of these enzyme-based systems was artificially increased by lowering the temperature below physiologically relevant values (i.e. to 0° C.).

From several practical perspectives, the fragile, high molecular weight enzyme-oligodeoxynucleotide conjugates described by Schultz et al are at an extreme disadvantage in comparison with Applicants' low molecular weight, stable, synthetic ribonuclease analogs.

Several practical points of Applicants' invention include the ability to prepare more than minute quantities of the agents; the ability to prepare high-purity material free from contaminating activities or unknown inactive impurities; the potential to survive in vivo conditions and to avoid immunological responses and the ability to avoid nonspecific hydrolysis of both DNA and RNA.

Applicants' use of hydrolysis as the chemical reaction that cleaves RNA provides several advantages over the prior art, such as the non-selective oxidative cleavage of both RNA and DNA taught by Chen et al. Applicants' hydrolysis agents are active at pH 7 which is consistent with the conditions inside living cells. Since DNA is chemically hydrolyzed at a considerably slower rate than RNA, the sequence-directed RNA hydrolysis using Applicants' oligodeoxynucleotide conjugates will not cleave their own oligodeoxy-nucleotide components at an appreciable rate. See Applicants' Example II below.

The term oligodeoxynucleotides used herein includes oligodeoxynucleotides and oligodeoxynucleotide analogs that are effective at molecular recognition by, for example, Watson-Crick or Hoogsteen base-pairing. Examples of such oligodeoxynucleotide analogs include those with nonionic internucleotide linkages such as alkylphosphotriesters, alkylphosphonates and alkylphosphoramidates (as described by P. S. Miller, *Oligodeoxynucleotides Antisense Inhibitors of Gene Expression*, J. S. Cohen, Ed. CRC Press, Boca Raton, Fla., 1989, Chapter 4 and references therein) and compounds with sulfur-containing internucleotide linkages such as phosphorothioates and phosphorodithioates (as described by C. A. Stein et al, ibid, Chapter 5 and references therein), and alpha-oligodeoxynucleotides (as described by B. Rayner et al, ibid, Chapter 6 and references therein). Other oligodeoxynucleotide analogs which may be suitable include those with internucleotide linkages such as carbonate, acetate, carbamate, dialkyl and diarylsilyl groups.

The compounds applicable to this invention are those metal complex conjugates and oligodeoxynucleotide conjugates which are soluble in water at a neutral pH and are functionally effective for the hydrolytic cleavage of RNA under physiologically relevant conditions. In their active forms, the metal complexes which hydrolyze RNA may contain hydroxyl or aquo ligands or both. These active forms may be derived in a standard fashion from complexes which contain ancillary ligands such as, chloride, bromide, iodide, perchlorate, nitrate, sulfate, phosphines, phosphites and other standard mono- and bidentate ligands. The metal in the metal complexes may be any metal which is effective in hydrolyzing RNA. Typical metals include copper, zinc, cobalt, nickel, palladium, lead, iridium, manganese, iron, molybdenum, vanadium, ruthenium, bismuth, magnesium, rhodium, uranium and the Lanthanide metals.

In order to provide the art a method of determining the applicable agents, such as metal complexes and conjugates of this invention, Applicants' have developed an assay for monitoring the hydrolysis of RNA under physiologically relevant conditions (7.1 pH and 37° C.).

APPLICANTS' ASSAY FOR HYDROLYSIS OF RNA

Figure 1B:
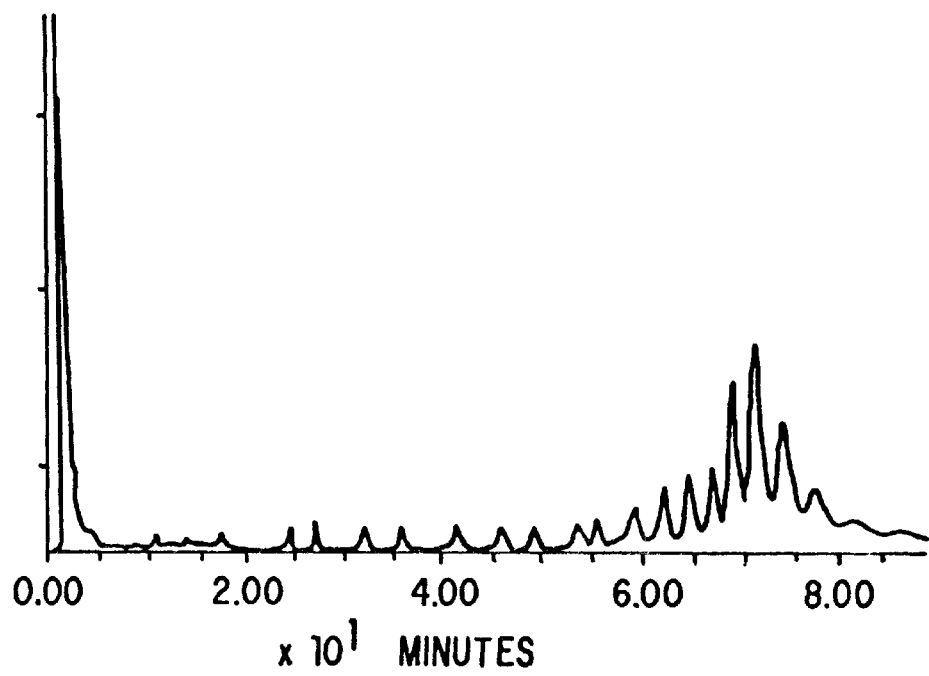

A mixture of adenylic acid oligomers 12 to 18 nucleotides in length [poly$(A)_{12-18}$] is used as the assay substrate. Ion exchange HPLC is used to resolve the individual cleavage products from the substrate fragments. A compound is determined to be active if it shows hydrolytic degradation of the substrate, as illustrated in FIG. 1, to an extent greater than that which is observed for a control reaction run under identical conditions in the absence of a cleavage agent. The extent of reaction is determined from the ratio of the integration of substrate peak at time=0 hour and time=18 hours.

HPLC analysis is performed with a Waters 600 multisolvent delivery system and a 490 programmable multiwavelength detector. Data is acquired on a NEC APC IV Advanced Personal Computer using Waters Maxima 820 software. With this system it is possible to determine the area under all the substrate peaks. Extensive standard precautions need to be taken to avoid RNase contamination: all buffers are made with diethylpyrocarbonate treated water (0.1% vol./vol.) and the reactions are run in sterilized polypropylene tubes. Typical stock solutions of RNA [poly$(A)_{12-18}$] having an adenosine concentration of 761 $\mu$M are prepared by dissolving 10 units of the RNA in 20 mM HEPES buffer pH=7.1. HPLC analyses are run on a 7 $\mu$M Nucleogen DEAE 60-7 with an elution gradient of 0–15 min. 25% B, 15–45 min. 60% B, 45–60 min. 100% B; using Solvent A=20 mM $KH_2PO_4$, 20% acetonitrile, pH=5.5; and Solvent B=Solvent A+1M KCl.

The combination of agents applicable and useful in this invention are those which functionally promote RNA hydrolysis as determined by this assay. The above described assay is not to be considered a limitation on Applicants' invention. It is to be understood that other assays can be developed and used to determine the effectiveness of agents for the hydrolysis of RNA in accordance with this invention.

A further check for the effectiveness of the metal complexes for hydrolyzing RNA is the formation of a conjugate. In forming such conjugates, the selected ligand may first be covalently linked to the desired nucleoside or nucleotide and then the selected metal ion attached to the ligand. Alternatively, the intact selected metal complex may be covalently linked to the nucleoside or nucleotide. The ligand or intact metal complex may be covalently linked to the nucleoside or nucleotide at any location. The details of forming specific conjugates are fully described in Applicants' Examples.

Likewise, in preparing the oligodeoxynucleotide conjugates of this invention, the selected ligand may first be covalently linked to the desired oligodeoxynucleotide and then the selected metal ion attached to the ligand. Alternatively, the intact selected metal complex may be covalently linked to the oligodeoxynucleotide. The ligand or metal complex can be covalently linked to the oligodeoxynucleotide at any location. The details of forming a specific oligodeoxynucleotide conjugate is fully described in Applicants' Example XIV.

EXAMPLES

The following Examples illustrate this invention (its compositions, processes and utility) with relation to specific metals, ligands, nucleosides, nucleotides and oligodeoxynucleotides. Specifics set forth in these Examples are not to be taken as limitations on the scope of the invention or to the applicable agents, elements or features of the invention.

Example I

This Example shows how metal complexes and other compounds are screened for RNA hydrolysis activity.

Stock solution (1 mM) of various transition metal complexes (shown in Table I) were prepared in 20 mM HEPES buffer pH=7.1. The assay mixture in a final volume of 1.5 mL contained 133 μM metal complex, 63 μM poly(A)$_{12-18}$ and 20 mM HEPES buffer. At time=0 hours a 200 μL of the mixture was removed and analyzed by Applicants' Assay. The reaction mixture was then incubated at 37° C. for 18 hours after which time a second 200 μL was removed and assayed. Summarized in Table I are the RNA hydrolysis active and inactive transition metal complexes and corresponding cleavage obtained as determined by Applicants' Assay.

TABLE 1

| Active | % Cleavage | Inactive | % Cleavage |
|---|---|---|---|
| Cu(trpy)$^{2+}$ | 75 | Cu(bpy)$_2$$^{2+}$ | 0 |
| Cu(bpy)$^{2+}$ | 43 | Ni-(CR)$^{2+}$ | 0 |
| Zn-N-Me-(CR)$^{2+}$ | 20 | [CuCR(CH$_2$)$_3$CuCR]$^{4+}$ | 0 |
| Cu-2, 2-CR$^{2+}$ | 22 | Cu(EDTA) | 0 |
| | | Zn(EDTA) | 0 |
| | | Zn(NTA)1$^{-1-}$ | 0 |

Abbreviations: trpy - 2,2':6',2"-terpyridine; bpy - 2,2'-bipyridine; N-Me-(CR) = 7-(N-methyl)-2,12-dimethyl-3,7,11,17-tetraazabicyclo[11.3.1]heptadeca-1 (17),2,11,13,15-pentaene; CR = 2,12-dimethyl-3,7,11,17-tetraazabicyclo [11.3.1]heptadeca-1 (17),2,11,13,15-pentaene; 2,2-(CR) = 2,10-dimethyl-3,6,9,12-tetraazabicyclo[9.3.1]pentadeca-1 (15),2,10,12,15-pentaene; EDTA = ethylenediaminetetraacetic acid; NTA = nitrilotriacetic acid; CR(CH$_2$)$_3$(CR) = 7,7'(1,3-propanediyl)-bis[2,12-dimethyl-3-7,11,17-tetraazabicyclo[11.3.1]heptadeca-1 (17),2,11,13,15-pentaene.

Summarized in TABLE 2 are compounds known to Applicants which are found not to be effective in RNA hydrolysis according to Applicants' Assay.

TABLE 2

| Compound | % Cleavage |
|---|---|
| 5 | 0 |
| 11 | 0 |
| 16 | 0 |
| 24 | 0 |
| 25 | 0 |
| 26 | 0 |
| 27 | 0 |

The identity and structure of the compounds in Table 2 are shown FIG. 8.

Example II

This Example shows that under conditions where a Cu(bpy)$^{2+}$ complex substantially hydrolyzes RNA, it does not degrade DNA.

The observed cleavage of RNA by various Cu(bpy)$^{2+}$ complexes was hydrolytic and not oxidative. This was demonstrated by comparing the reactivity of the Cu(bpy)$^{2+}$ complexes with both DNA and RNA. A stock solution of DNA [poly(dA)$_{12-18}$] was prepared by dissolving 25 units of the DNA in 1.0 mL of 20 mM HEPES buffer pH=7.1. The reaction mixture contained in a total volume of 1.5 mL, 63 μM of the DNA, 157 μM bipyridine, 157 μM CuCl$_2$ and 20 mM HEPES buffer. The solutions were incubated at 37° C. for 48 hours after which time they were assayed by ion exchange HPLC. Identical conditions were used in the reaction of the Cu(bpy)$^{2+}$ complex with RNA[poly(A)$_{12-18}$].

FIG. 6 contains the HPLC analysis of the reactions of the Cu(bpy)$^{2+}$ complexes with the DNA and RNA. After 48 hours the RNA is extensively hydrolyzed. By contrast, the DNA substrate showed no evidence of degradation. It has been reported that both RNA and DNA are oxidatively cleaved by 1,10-phenathroline-copper(II) at similar rates (C. B. Chen et al, *J. Am. Chem. Soc.* 1988, 110, 6570–6572). Consequently, one would expect to see extensive cleavage of the DNA by the Cu(bpy)$^{2+}$ complex if an oxidative mechanism was operative.

Example III

This Example shows the attachment of bipyridyl ligand (bpy) to the 3' position of 2'-deoxy-thymidine nucleotide as outline in Scheme 1.

5'-O-DMT-2'-deoxy-thymidine-3'-O-β-cyanoethyl N,N-diisopropyl phosphoramidite (1) (0.4 gm., 0.537 mmol) was dissolved in anhydrous CH$_3$CN (5 mL) under N$_2$ and tetrazole (0.112 gm., 1.61 mmol) was added. DMT is 4,4'-dimethoxytrityl. The resulting mixture was stirred at room temperature for 15 minutes. An acetonitrile solution (5 mL) of 4'-methyl-4-(hydroxybutyl)-2,2'-bipyridine (2) (0.130 gm., 0.540 mmol) was added and after 1 hr. the mixture was concentrated in vacuo to yield a glass of compound 5'-O-DMT-2'-deoxy-thymidine-3'-O-[4-[4'-methyl(2,2'-bipyridin)- 4-yl]butoxy]-β-cyanoethoxyphosphine (3). Compound (3) was dissolved in CH$_2$Cl$_2$ (3 mL), cooled to 0° C. in an ice bath and t-BuOOH in 2,2,4,4-tetramethylpentane (0.643 mL, 1.93 mmol) was added. After 20 min. the mixture was concentrated in vacuo to yield a glass of 5'-O-DMT-3'-[4-[4'-ethyl(2,2'-bipyridin)-4-yl]butyl-β-cyanoethyl phosphate]-2'-deoxy-thymidine (4). Compound (4) (0.382 gm., 0.432 mmol, 80.4%) was eluted from an Alumina column (neutral) using 5% MeOH in CH$_2$Cl$_2$.

Compound (4) (0.382 gm., 0.432 mmol) was dissolved in aqueous NH$_3$ (10 mL) and left to stir at room temperature for 6 hours. The mixture was concentrated in vacuo using EtOH to remove water. The residue was treated with 25% CF$_3$COOH in CH$_2$Cl$_2$ (5 mL) for 15 minutes. After removing the volatile components in vacuo the residue was dissolved in water (10 mL) and the aqueous layer washed with ether (2×5 mL) and CH$_2$CL$_2$ (2×5 mL). The aqueous layer was concentrated in vacuo to yield the desired deprotected nucleoside 3'-[4-[4'-methyl(2,2'-bipyridin)-4-yl]butyl-phosphate]-2'-deoxy-thymidine ammonium salt (5) (0.192 gm., 0.354 mmol, 82%).

Example IV

Figure 2:
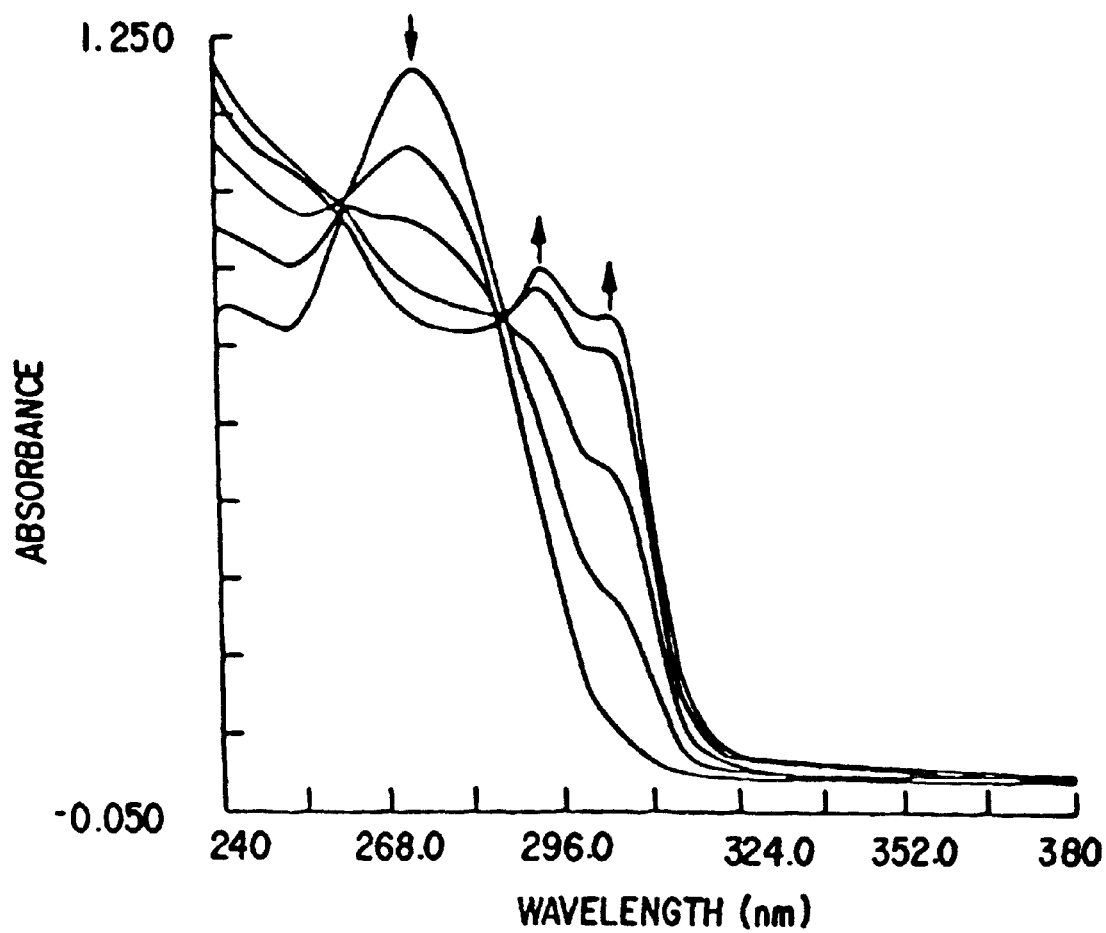
In FIG. 2 there is shown the titration of 3'-[4-[4'-methyl (2,2'-bipyridin)-4-yl]butyl-phosphate]-2'-deoxy-thymidine ammonium salt (5) with $CuCl_2$ forming 3'-[4-[4'-methyl(2, 2'-bipyridin)-4-yl]butyl-phosphate]-2'-deoxy-thymidine ammonium salt copper(II) (6). This Figure depicts Applicants' Example IV and demonstrates the formation of a metal complex nucleotide conjugate in accordance with Applicants' invention.

This Example shows the titration of compound (5) with CuCl$_2$ to form 3'-[4-[4'-methyl(2,2'-bipyridin)-4-yl]butyl-phosphate]-2'-deoxy-thymidine ammonium salt copper(II) (6) (FIG. 2).

A 1 mL aliquot of a 53.4 μM solution of compound (5) in 20 mM HEPES buffer having a pH of 7.1 is placed in a quartz cuvette and aliquots of a 1.178 mM stock solution of CuCl$_2$ in water was added. Changes in the visible spectrum were monitored between the wavelength of 240 and 380 nm. The addition of CuCl$_2$ causes the band at 276 nm to decrease with concomitant increase in absorbances at 302 and 312 nm. The changes occur with an isosbestic pint at 289 nm and are characteristic of coordination of Cu$^{2+}$ to bipyridine.

A similar titration with the solution of 3'-thymidine monophosphate without the bipyridine ligand showed no changes in the visible spectrum over the noted region.

Example V

Figure 3A:
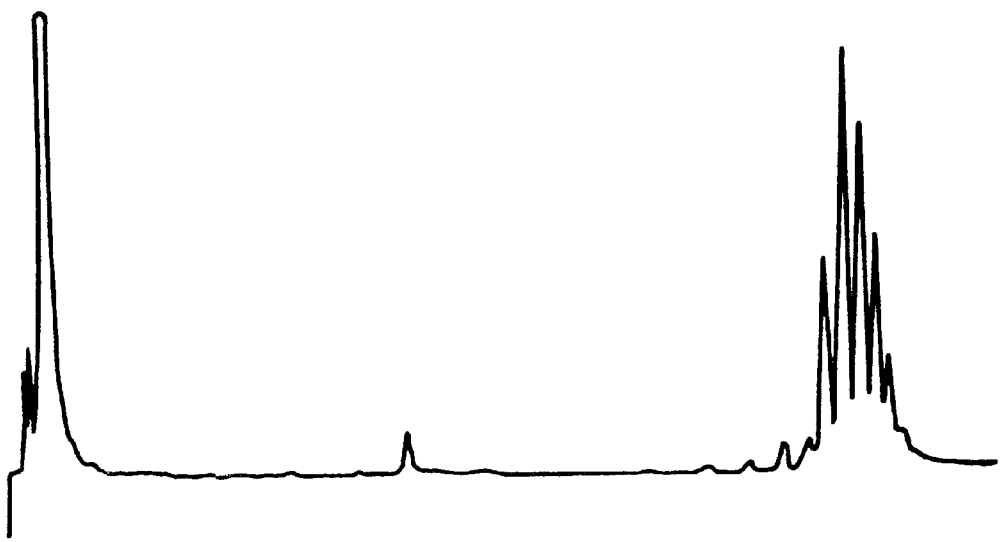
In FIG. 3 there is shown the hydrolytic cleavage of RNA [poly(A)$_{12-18}$] by compound (6). This Figure depicts Applicants' Example V and demonstrates that a metal complex linked to the 3' position of a nucleotide is capable of hydrolyzing RNA. A, Control reaction, time=48 hours; B, Reaction of (6) with RNA, time=48 hours.
Figure 3B:
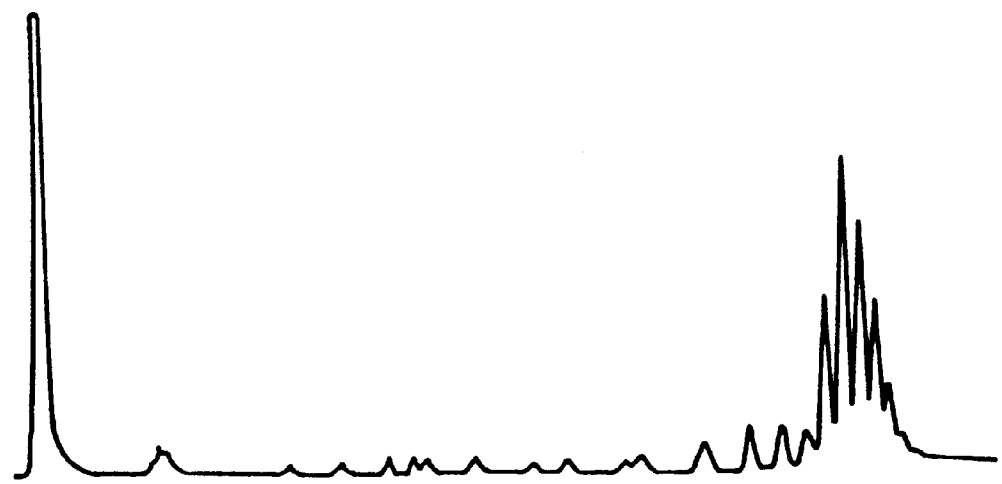

This Example shows the hydrolysis of RNA [poly(A)$_{12-18}$] by a nucleotide covalently linked through the 3' position to a metal complex (FIG. 3).

For the reactions of metal complex-nucleotide (nucleoside) conjugates, Applicants' HPLC Assay described above was modified. These compounds are not as reactive as the free metal complexes, thus, the reaction time was extended to 48 hours.

In a total of 500 $\mu$L, the reaction mixture contained 157 $\mu$M of compound (5), 63 $\mu$M RNA, 157 $\mu$M Cu(SO$_4$) and 20 mM HEPES buffer pH=7.1. Using this mixture, compound (6) was formed under the conditions set forth in Example IV. At time zero, a 100 $\mu$L aliquot of the reaction mixture was removed and immediately analyzed by Applicants' HPLC Assay. The reaction mixture was incubated at 37° C. for 48 hours after which time a second aliquot was removed and assayed. It was found that the RNA substrate was clearly hydrolyzed by compound (6) (FIG. 3).

A control reaction carried out in the same manner except in the absence of the Cu(SO$_4$) showed no hydrolysis of the RNA even after the 48 hour incubation.

Example VI

This Example shows the attachment of bipyridyl ligand (bpy) to the 5' position of 2'-deoxy-thymidine nucleotide as outlined in Scheme 2.

Preparation of 5'-[4-[4'-methyl(2,2'-bipyridin)-4-yl]butyl]-methylphosphate-3'-O-acetyl-2'-deoxy-thymidine (10): a mixture of 4-[4'-methyl(2,2'-bipyridin)-4-yl]butyl-methyl-N,N-diisopropyl phosphoramidite (8) (0.101 gm., 0.25 mmol) and tetrazole in 1 mL of THF was stirred at room temperature for 10 minutes. 3'-O-acetyl-2'-deoxythymidine (7) (0.071 gm., 0.25 mmol) dissolved in CH$_2$Cl$_2$ (1 mL) was added to the reaction mixture and the solution was left stirring for 60 minutes. The mixture was then filtered to remove tetrazole which precipitated out. The solid was washed with acetonitrile (5 mL) and CH$_2$Cl$_2$ (5 mL) and concentrated to yield 5'-O-[[4-[4'-methyl(2,2'-bipyridin)4-yl]butoxy]methoxy]-3'-O-acetyl-phosphine-2'-deoxy-thymidine (9) as a glass. The compound (9) glass was dissolved in MeOH (1 mL), cooled to 0° C. and a 3M solution of t-butyl hydroperoxide in 2,2,4,4-tetramethylpentane (0.3 mL, 0.9 mmol) was added to the stirred reaction mixture. After 15 min. the ice bath was removed and the mixture stirred at room temperature for 20 minutes. The mixture was concentrated to a glass and flash chromatographed on an alumina column (TLC grade). The desired compound (10) (0.071 gm., 0.118 mmol, 47%) eluted off the column using a gradient of CH$_2$Cl$_2$ to 10% MeOH in CH$_2$Cl$_2$ as an eluant.

Preparation of 5'-[4-[4'-methyl(2,2'-bipyridin)-4-yl]butylphosphate]-2'-deoxy-thymidine triethylammonium salt (11): to compound (10) (0.071 gm., 0.118 mmol) dissolved in CH$_2$Cl$_2$ (3 mL); 25% NaOMe in MeOH (0.05 mL, 0.12 mmol) was added. The mixture was stirred for 15 min. at room temperature. After 15 min. the reaction was quenched with glacial acetic acid (0.06 gm., 0.12 mmol). Dichloromethane (50 mL) was added and the organic layer washed with saturated NaHCO$_3$ solution (2×20 mL) and water (10 mL). The organic layer was dried over anhydrous Na$_2$SO$_4$ and concentrated in vacuo to a glass (0.064 gm., 0.114 mmol, 97%). The glass was dissolved in 0.5 mL thiophenol:dioxane:triethylamine (1:2:2), a commercial deprotection reagent by Sigma Chemicals, and left to stir for 90 minutes. The mixture was concentrated in vacuo to a glass and the residue dissolved in water (10 mL). The aqueous layer was washed with petroleum ether (2×10 mL) to remove traces of thiophenol. Final purification was carried out by RP C-18 Sep-Pak column and eluting the desired compound (11) (0.069 gm., 0.106 mmol, 90%) with H$_2$O:CH$_3$CN (4:1).

Example VII

This Example shows the titration of compound (11) prepared in Example VI with CuCl$_2$ to form 5'-[4-[4'-methyl (2,2'-bipyridin)-4-yl]-butyl-phosphate]-2'-deoxy-thymidine triethylammonium salt copper(II) (12).

The procedure described in Example II was followed. Changes in visible spectrum, similar to those shown in FIG. 3, characteristic of coordination of copper(II) to bipyridine were observed. Titration of thymidine-5'-monophosphate showed no changes in the visible spectrum over the range 240–380 nm.

Example VIII

This Example shows the hydrolysis of RNA [poly(A)$_{12-18}$] by a nucleotide covalently linked through the 5' position to a transition metal complex.

Figure 4A:
In FIG. 4 there is shown the hydrolytic cleavage of RNA [poly(A)$_{12-18}$] by 5'-[4-[4'-methyl(2,2'-bipyridin)-4-yl] butyl-phosphate]-2'-deoxy-thymidine triethylammonium salt copper(II) (12). This Figure depicts Applicants' Example VIII and demonstrates that a metal complex linked to the 5' position of a nucleotide is capable of hydrolyzing RNA. A, Control reaction, time=48 hours; B, Reaction of (12) with RNA, time=48 hours.
Figure 4B:
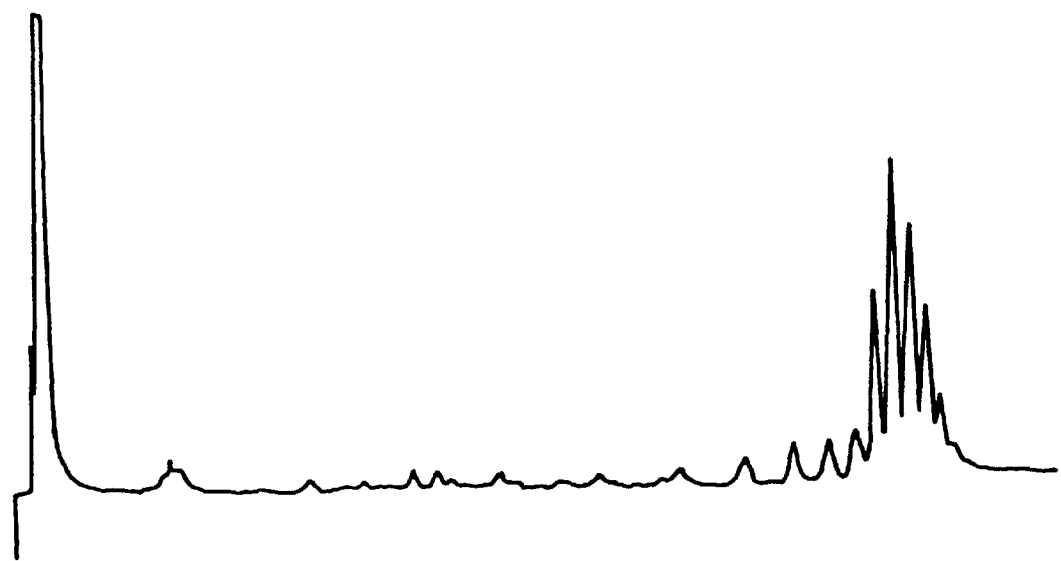

An identical procedure was used as described in Example IV except that compound (12) was the hydrolysis agent (FIG. 4).

Example IX

This Example shows the attachment of bipyridyl ligand (bpy) to the 5-position of the uracil in a uridine nucleoside as outlined in Scheme 3.

Preparation of 5'-O-DMT-5-[3-[[2-[[4-[4'-methyl [2,2'-bipyridin]-4-yl]-1-oxobutyl]amino]ethyl]amino]-3-oxopropyl]-2'-deoxy-uridine (15): a solution of 5-[3-[(2-aminoethyl)amino]-3-oxopropyl]-5'-O-DMT-deoxy-uridine (13) (0.322 gm, 0.5 mmol) in CH$_3$CN (5 mL) and Et$_3$N (0.2 mL) was cooled to 0° C. in an ice bath and 4-[3-carbo-3-(p-nitrophenoxy)propyl]-4'-methyl-2,2'-bipyridine (14) (0.566 gm, 1.5 mmol) was added to the stirred reaction mixture. After 15 min. the ice bath was removed and the mixture was stirred at room temperature for 24 hours. The reaction mixture was diluted with 20 mL CH$_2$Cl$_2$ and water (10 mL). The aqueous layer was washed with CH$_2$Cl$_2$ (2×20 mL). The dried (MgSO$_4$) organic layer was concentrated in vacuo and flash chromatographed on an alumina (neutral) column eluting with a gradient of CH$_2$Cl$_2$ to 6% EtOH in CH$_2$Cl$_2$ to remove p-nitro-phenol. The desired product eluted off the column using EtOH along with C-3 bpy acid. Compound (15) (0.211 gm., 0.24 mmol, 45%) was purified by RP HPLC using a linear ternary gradient flowing at 6 mL/minute. Solvent A (0.1M) [Et$_3$NH]OAc was kept constant while MeCN and H$_2$O were varied.

Preparation of 5-[3-[[2-[[4-[4'-methyl[2,2'-bipyridin]-4-yl]-1-oxobutyl]amino]ethyl]amino]-3-oxopropyl]-2'-deoxy-uridine (16): a solution of the nucleoside (15) (0.150 gm., 0.17 mmol) in CH$_2$Cl$_2$ (5 mL) was treated with 10% CF$_3$COOH in CH$_2$Cl$_2$ (5 mL) for 15 minutes. The mixture was concentrated to a glass and dissolved in water (10 mL). The aqueous layer was washed with CH$_2$Cl$_2$ (2×10 mL) and compound (16) (0.093 gm., 0.16 mmol, 94%) was purified by RP HPLC using a linear ternary gradient flowing at 6 mL/minute. Solvent A (0.1M) [Et$_3$NH]OAc was kept constant while MeCN and H$_2$O were varied.

Example X

This Example shows the titration of compound (16) with CuCl$_2$ to form 5-[3-[[2-[[4-[4'-methyl[2,2'-bipyridin]-4'-yl]-1-oxobutyl]amino]ethyl]amino)-3-oxopropyl]-2'-deoxy-uridine copper(II) (17).

The procedure described in Example III was followed. Changes in visible spectrum similar to those shown in FIG. 2 and characteristic of coordination of copper(II) to bipyridine were observed. Titration of uridine showed no changes in the visible spectrum over the range 240–380 nm.

Example XI

This Example shows the hydrolysis of RNA [poly (A)$_{12-18}$] by a metal complex covalently linked through the 5-position of uracil in a uridine nucleoside.

Figure 5A:
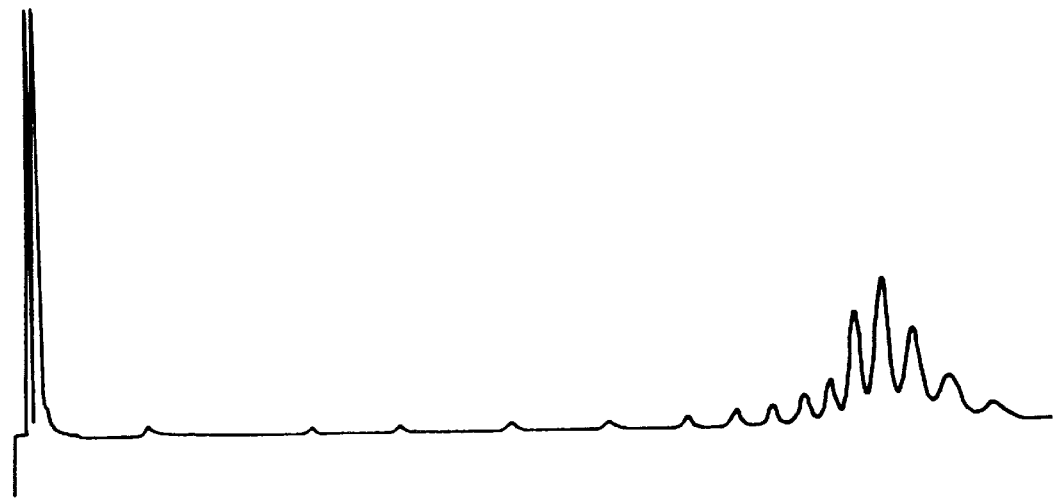
In FIG. 5 is shown the hydrolytic cleavage of RNA [poly(A)$_{12-18}$] by 5'-[3-[[2-[[4-[4'-methyl[2,2'-bipyridin]-4-yl]-1-oxobutyl]amino]ethyl]amino]-3-oxopropyl]-2'-deoxy-uridine copper(II) (17). This Figure depicts Applicants' Example XI and demonstrates that a metal complex linked to the base portion of a nucleoside is capable of hydrolyzing RNA. A, Control reaction, time=48 hours; b, Reaction of (17) with RNA, time=48 hours.
Figure 5B:
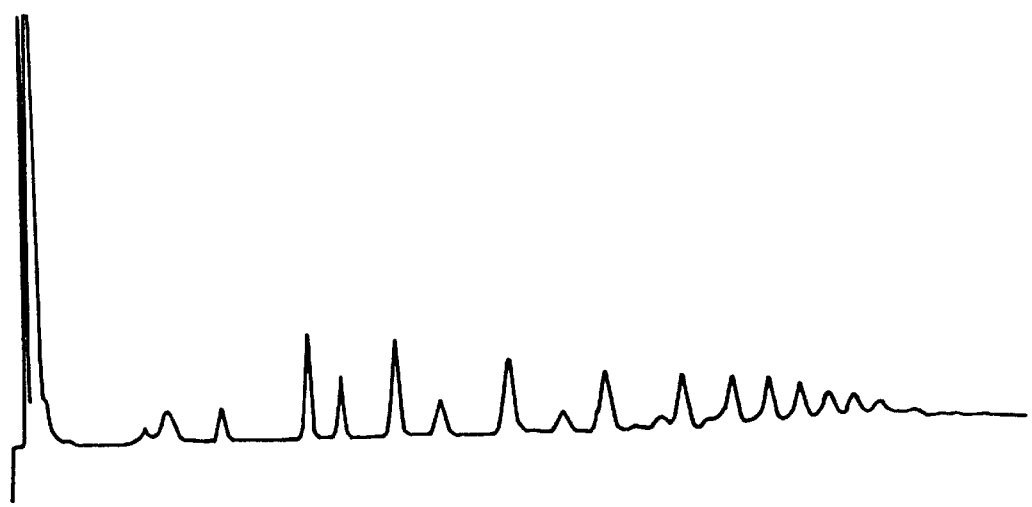
Figure 6A:
In FIG. 6 there is shown the reaction of the Cu(bpy)$^{2+}$ complex with both DNA [poly(dA)$_{12-18}$] and RNA [poly (A)$_{12-18}$]. This Figure depicts Applicants' Example II and demonstrates that the observed cleavage of RNA by the Cu(bpy)$^{2+}$ complex is hydrolytic in nature and not oxidative. A, Control reaction with DNA, time=18 hours; B, Reaction of the Cu(bpy)$^{2+}$ with DNA, time=18 hours; C, Control reaction with RNA, time=18 hours; D, Reaction of the Cu(bpy)$^{2+}$ complex with RNA, time=18 hours.
Figure 6B:
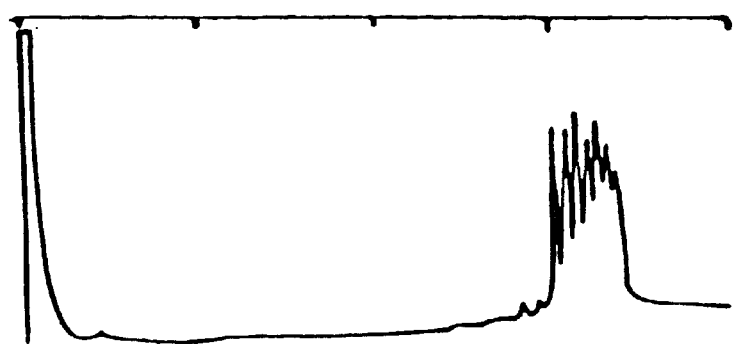
Figure 6C:
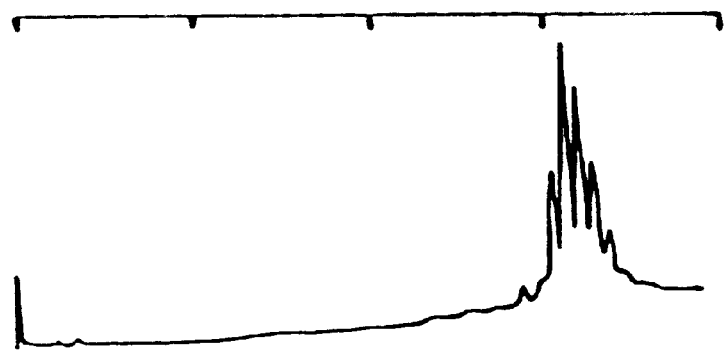
Figure 6D:
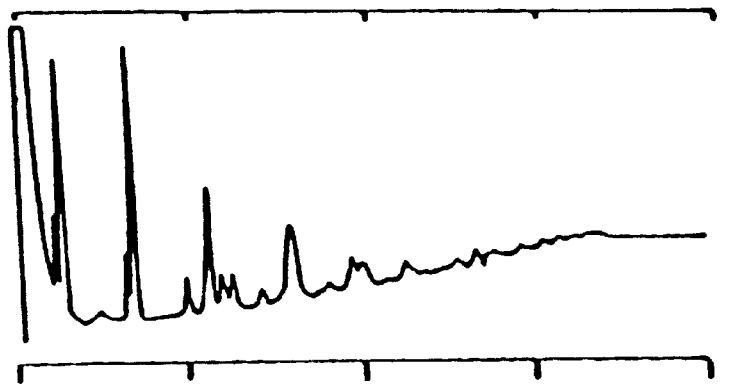
Figure 7A:
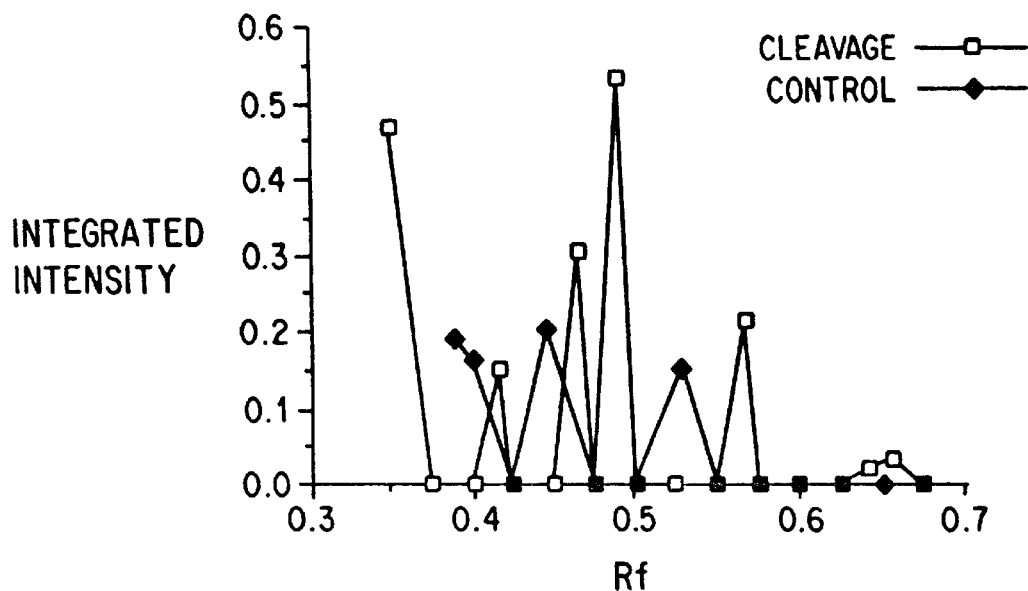
In FIG. 7 there is shown the densitometry results of polyacrylamide gel electrophoresis analysis of the sequence-directed hydrolysis of tRNA$^{Tyr}$ by the oligodeoxynucleotide-Cu(bpy)$^{2+}$ conjugate (32). This Figure depicts Applicants' Example XV showing Densitometry scans of the polyacrylamide gel of the reaction of (32) with tRNA$^{Tyr}$ after 17 hours under the conditions described in Example XV and of the control reaction. A, Cleavage Reaction: 1.29 $\mu$M tRNA$^{Tyr}$, 6.4 $\mu$M (31), 12.9 $\mu$M Cu (trpy)$^{2+}$, 227 $\mu$M Cu(SO$_4$), 50 mM NaCl and 50 mM Tris buffer pH=7.8; Control Reaction: 1.29 $\mu$M tRNA$^{Tyr}$, 12.9 $\mu$M Cu(trpy)$^{2+}$, 227 $\mu$M Cu(SO$_4$), 50 mM NaCl and 50 mM Tris buffer pH=7.8; B, Cleavage Reaction: 1.29 $\mu$M tRNA$^{Tyr}$, 6.4 $\mu$M (31), 12.9 $\mu$M Cu(trpy)$^{2+}$, 227 $\mu$M Cu(SO$_4$), 50 mM NaCl and 50 mM Tris buffer pH=7.8; Control Reaction: 1.2 $\mu$M tRNA$^{Tyr}$, 12.9 $\mu$M Cu(trpy)$^{2+}$, 227 $\mu$M Cu(SO$_4$) and 6.4 $\mu$M 14 mer-oligodeoxynucleotide 5'-HO-TGACGGCAGATTTA-OH-3'.
Figure 7B:
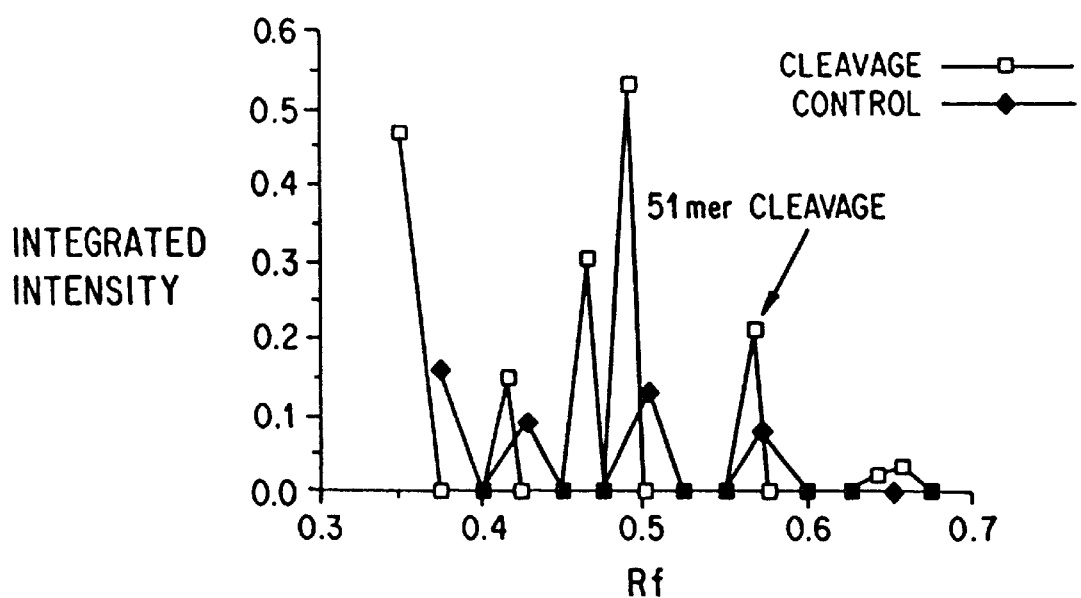
Figure 8A:
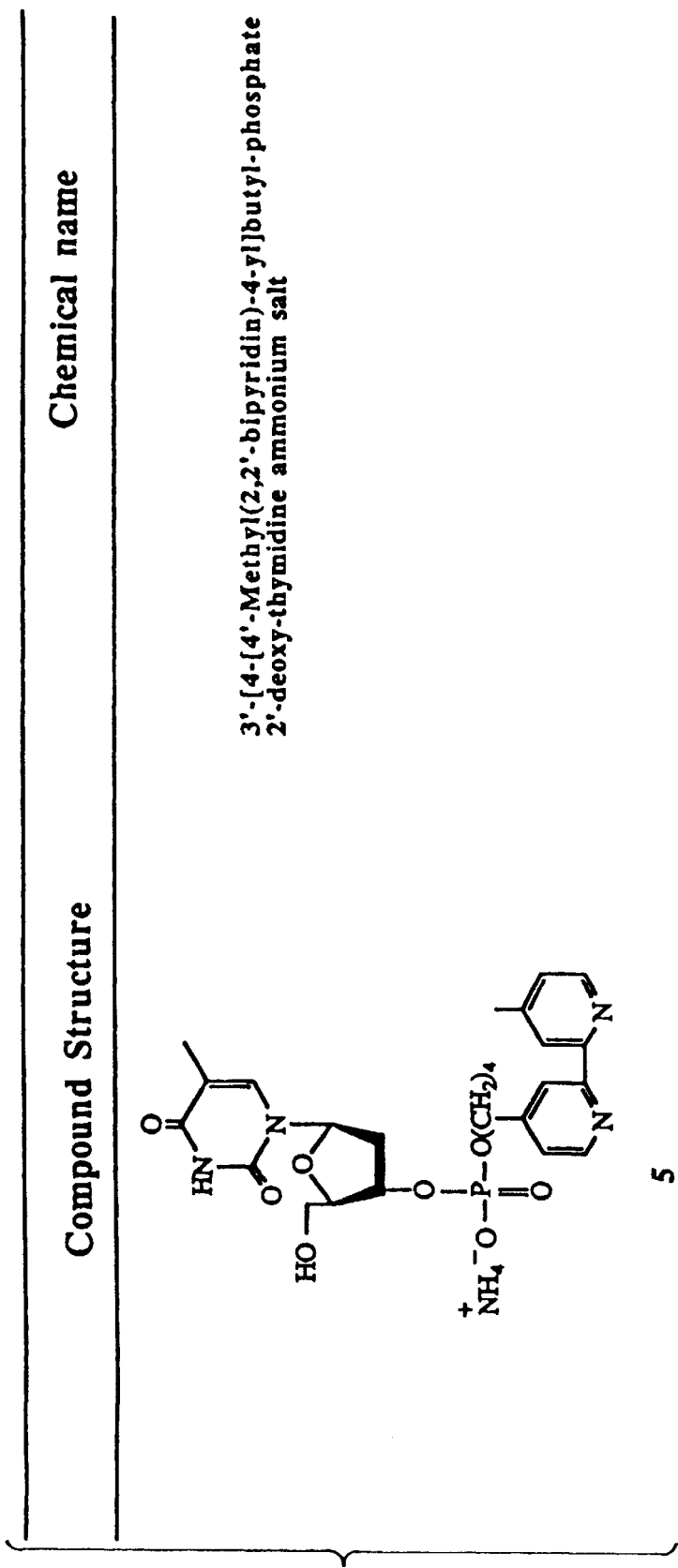
In FIG. 8 is shown the structure and identity of compounds known to Applicants which do not show RNA hydrolysis according to this invention.
Figure 8C:
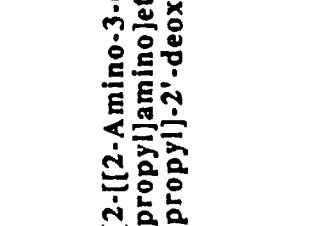
Figure 8D:
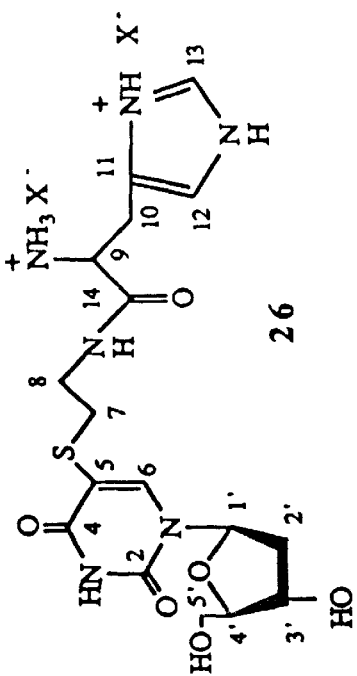
Figure 8D:
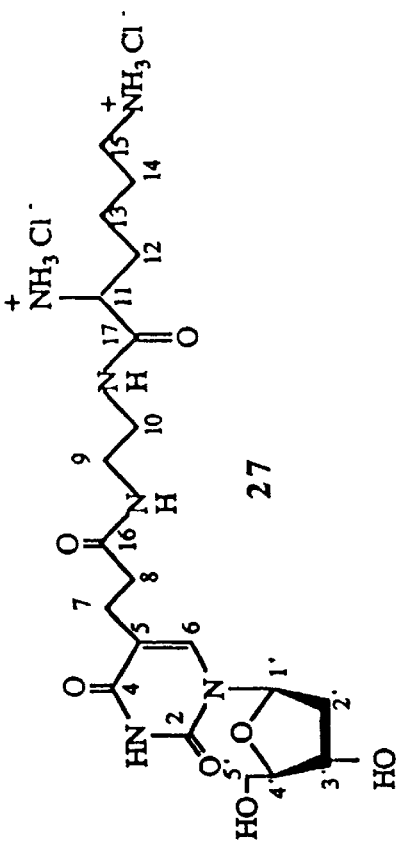

An identical procedure was used as described in Example IV except that compound (17) was the hydrolysis agent. Hydrolysis of the RNA is evident as shown in FIG. 5.

Example XII

This Example shows the preparation of various terpyridine (trpy) derivatives (Scheme 4) which can be attached to nucleotides as described in Examples IV and V and which have been previously shown in Example I to be active RNA hydrolysis catalysts.

Preparation of 4'-(3-formylpropyl)-2,2':6',2"-terpyridine (19): a 100 mL three necked RB flask, equipped with a rubber septum, a teflon coated stir bar and a gas inlet adaptor was flushed with $N_2$. 4'-methyl-2,2':6',2"-terpyridine (18) (0.494 gm., 2 mmol), prepared by literature methods (see K. T. Potts, et al, *J. Am. Chem. Soc.*, 1987, 109, 3961–3967) was dissolved in dry THF (10 mL) and was syringed into the flask. The reaction mixture was cooled to −78° C. and LDA (1.6 mL, 2.4 mmol) was added via syringe. The resulting dark brown mixture was stirred for 2 hr. at −78° C. 2-(2-bromoethyl)-1,3-dioxolane (0.434 mL, 2.4 mmol) was syringed into the reaction mixture, stirred for 1 hr. at −78° C. and allowed to warm to room temperature overnight. The mixture was poured over 10 ml brine and the aqueous layer was extracted with $CH_2Cl_2$. The extracts were dried over $MgSO_4$ and evaporated to dryness to yield the crude acetal. The acetal was hydrolyzed with 1M HCl (10 mL) by heating to 50–60° C. for 2 hours. The solution was then neutralized with aqueous $NaHCO_3$ and extracted with $CH_2Cl_2$. The extracts were dried over $MgSO_4$ and evaporated to dryness to yield the crude aldehyde. Purification by flash chromatography (neutral alumina, $CH_2Cl_2$ elution) gave pure aldehyde (19) (0.339 gm., 1.12 mmol, 56%).

Preparation of 4'-(4-hydroxybutyl)-2,2':6',2"-terpyridine (20): the aldehyde (19) (0.303 gm., 1 mmol) was dissolved in absolute ethanol (5 mL) and sodium borohydride (0.05 gm., 1 mmol) was added at room temperature. After stirring for 30 min. the mixture was poured into 10 mL brine and extracted with $CH_2Cl_2$ (3×10 mL). The extracts were dried over $MgSO_4$ and evaporated to dryness to yield the desired alcohol (20) (0.264 gm., 0.86 mmol, 86%).

Compound (20) is analogous to compound (2) in Scheme 1 and can be attached to the 3' position of thymidine in a similar fashion as described in Example II.

Preparation of 4'-(4-bromobutyl)-2,2':6',2"-terpyridine (21): the alcohol (20) (0.200 gm., 0.65 mmol) was dissolved in 5 mL HBr (45%) and refluxed for 6 hours. After cooling to room temperature the mixture was poured over 20 gm. of crushed ice, basified with saturated aqueous solution of $Na_2CO_3$ and extracted with $CH_2Cl_2$. The extracts were dried over ($MgSO_4$) and evaporated to dryness to yield the bromo derivative (21) (0.186 gm., 0.51 mmol, 78%).

Preparation of 4'-(4-phthalimidobutyl)-2,2':6',2"-terpyridine (22): the bromo compound (21) (0.186 gm., 0.51 mmol) in DMF (2 mL) was added to a suspension of potassium phthalimide (0.095 gm., 0.51 mmol) in DMF (1 mL). The mixture was stirred for 2 hr. at 50–60° C. After cooling the reaction mixture was poured into water (10 mL) and the resulting mixture was thoroughly extracted with $CHCl_3$ (3×25 mL). The organic layers were combined, washed with 20 mL of 0.2 M NaOH, water (20 mL) and dried over $Na_2SO_4$. Removal of solvent under reduced pressure gave a thick oil. Recrystallization from ethanol gave compound (22) as a white crystalline solid (0.208 gm., 0.48 mmol, 95%) mp 128° C.

Preparation of 4'-(4-aminobutyl)-2,2'1:6'2"-terpyridine (23): phthalimide derivative (22) (0.208 gm., 0.48 mmol) was suspended in 7 mL EtOH and treated with hydrazine hydrate (88 mg., 0.48 mmol). The mixture was refluxed for 6 hr., cooled to room temperature, poured into brine (10 mL) and basified with 50% w/w NaOH to pH 12. The mixture was thoroughly extracted with $CH_2Cl_2$ (3×10 mL). The organic layers were dried over $Na_2SO_4$. Removal of solvent under reduced pressure gave the desired product (23) (0.130 gm., 0.43 mmol, 89%).

Compound (23) can be attached to the 5' position of 2'-deoxy-thymidine by literature procedures (see B. C. F. Chu et al, DNA 1985, 4, 327–331).

Example XIII

This Example shows a variety of nucleosides and nucleotides which have groups appended on the 3' and 5' position of 2'-deoxy-thymidine and 5-position uracil in 2'-deoxy-uridine and which are not active at hydrolyzing RNA [poly(A)$_{12-18}$] under the conditions of the HPLC assay (Table 2).

No hydrolysis of the RNA was observed with the compounds shown in Table 2 when assayed in the absence of $Cu(SO_4)$ under the conditions described in Example IV.

Example XIV

This Example shows the attachment of bipyridine ligand to a 14 mer oligodeoxynucleotide (30) as shown in Scheme 5.

Preparation of 4-(3-carbo-N-hydroxysuccinimidopropyl)-4'-methyl-2,2'-bipyridine (29): 4-(3-carboxypropyl)-4'-methyl-2,2'-bipyridine (28) (1.0 gm., 3.9 mmol) and N-hydroxysuccinimide (0.494 gm., 4.3 mmol) were dissolved in EtOAc (10 ML) and the mixture was cooled to 0° C. in an ice bath. Compound (28) was prepared in accordance with the teachings of L. Ciana et al, *J. Org. Chem.* 1989, 54, 1731–1735. Dicyclohexylcarbodiimide (DCC) (0.804 gm., 3.9 mmol) was added in small portions and the mixture was stirred at 0° C. for 30 minutes. The ice bath was removed and the mixture was allowed to stir at room temperature for 12 hours. The resulting precipitate was filtered off and the filtrate concentrated in vacuo. The residue was dissolved in $CH_2Cl_2$ (100 mL), washed with water (50 mL) and dried over $Mg(SO_4)$. The dried organic extract was concentrated in vacuo to yield compound (29) (0.827 gm., 2.3 mmol, 59%).

Preparation of oligodeoxynucleotide-bipyridine conjugate (31): to an aqueous solution (20 mL) of the oligodeoxynucleotide (30) was added a solution of compound (29) in $CH_3CN$ (20 mL). The pH of the mixture was raised to 9.3 by the addition of $Et_3N$ and the mixture was stirred overnight. The oligodeoxynucleotide-bipyridine conjugate (31) was purified by anion exchange HPLC.

Example XV

This Example shows a sequence-directed cleavage of tRNA$^{Tyr}$ by an oligodeoxynucleotide-bipyridine copper(II) (32) complex in accordance with this invention as outlined in Scheme 6.

A 101 μM stock solution of oligodeoxynucleotide-bipyridine conjugate (31) was prepared by dissolving 6.1 units of compound (31) in 500 μL of 20 mM HEPES buffer having a pH of 7.1. A 25.9 μM stock solution of the tRNA$^{Tyr}$ substrate was prepared by dissolving 10 Units of tRNA$^{Tyr}$ in 500 μL of 20 mM HEPES buffer having a pH of 7.1. The cleavage reaction contained in a total of 600 μL, 1.29 μM tRNA$^{Tyr}$, 12.9 μM Cu(trpy)$^{2+}$, 227 μM Cu(SO$_4$), 6.4 μM compound (31), 50 mM NaCl and 50 mM HEPES buffer having a pH of 7.8. Initially the tRNA$^{Tyr}$, compound (31), NaCl and buffer were combined and heated to 65° C. for 4 min. in a water bath. The reaction was removed and immediately placed on dry ice. The mixture was allowed to thaw at 0° C. after which time the Cu(SO$_4$) and the Cu(trpy)$^{2+}$ complex were added. Applicants have shown in Example III that the copper(II) coordinates to the bipyridine ligand exclusively forming in this case the oligodeoxynucleotide-metal complex conjugate (32). The reaction was heated at 37° C. and 100 μL aliquots were removed at times=0, 17 and 28 hours. Analysis of the aliquots by polyacrylamide gel electrophoresis revealed three distinct cleavage sites adjacent to the targeted sequence as shown in FIG. 6. These bands appeared in a time-dependent fashion and control reactions were devoid or showed significantly reduced cleavage in these regions.

The predicted position of RNA cleavage based on the hybridization of compound (32) to tRNA$^{Tyr}$ would produce a fragment 51 nucleotides in length (Scheme 5). This fragment was observed. Two other fragments also appear from the reaction. These are attributed to cleavage at sites brought close to the reactive group in compound (32) due to three dimensional folding of the tRNA$^{Tyr}$ molecule. Thus, sequence-directed cleavage of tRNA$^{Tyr}$ was demonstrated.

SCHEME 1

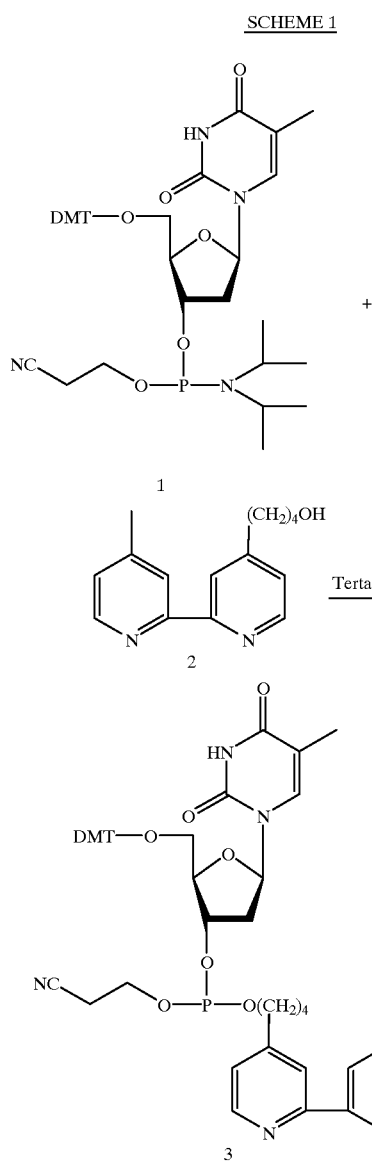

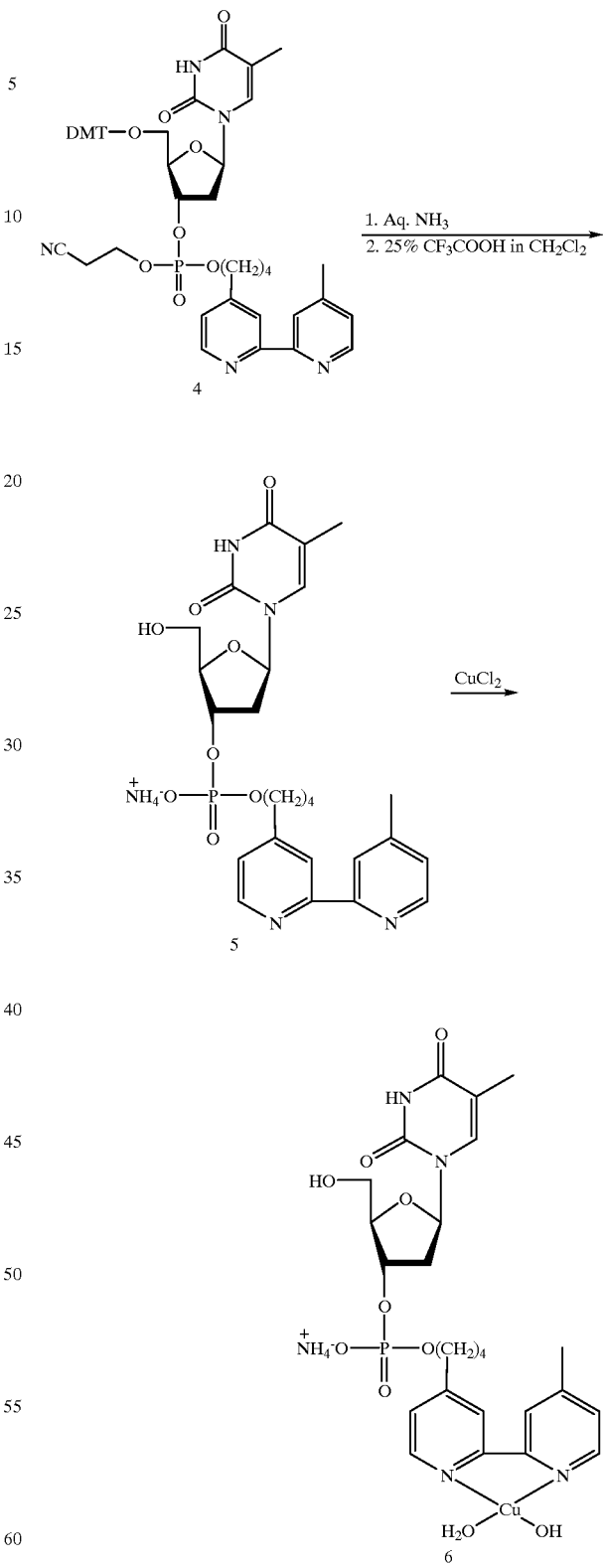

SCHEME 2
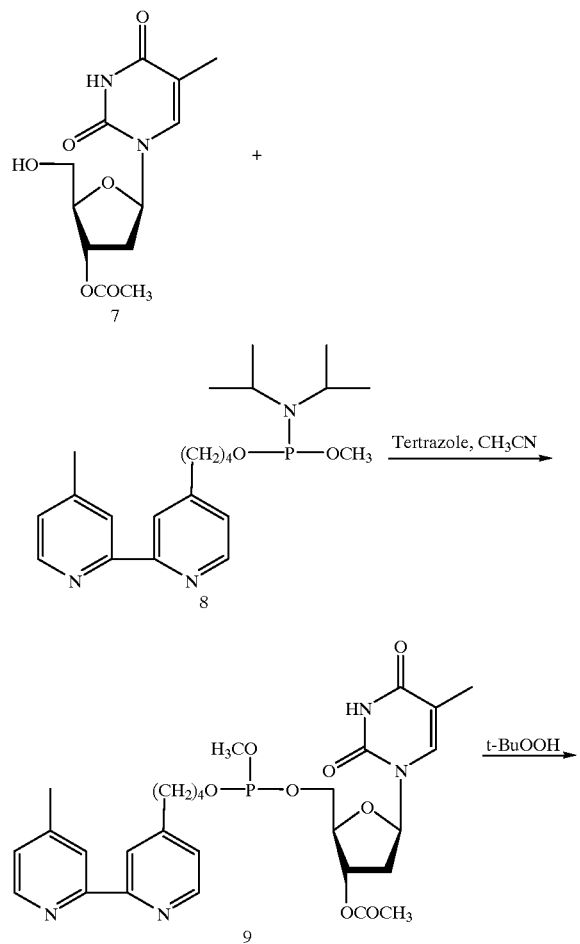
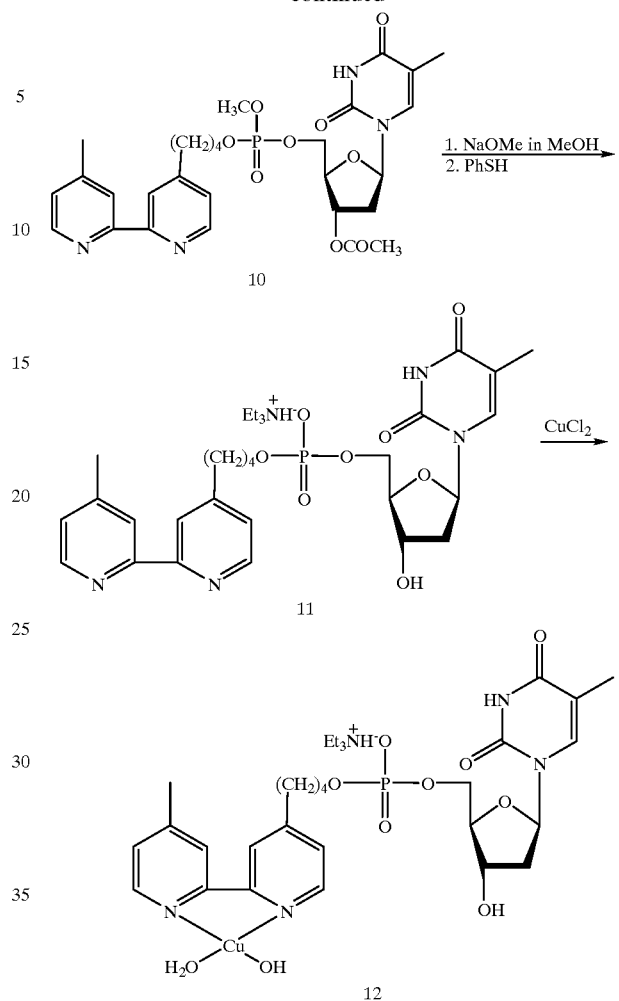
SCHEME 3
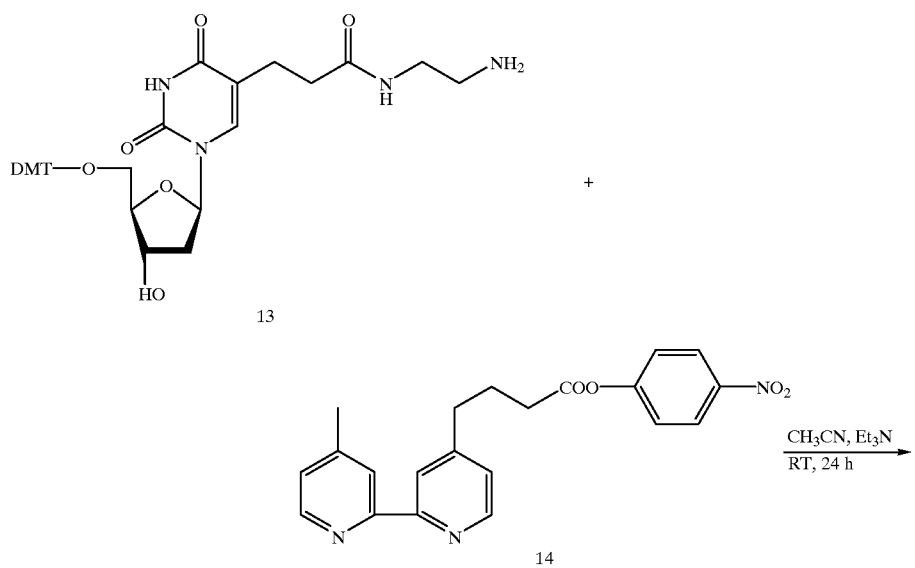

-continued
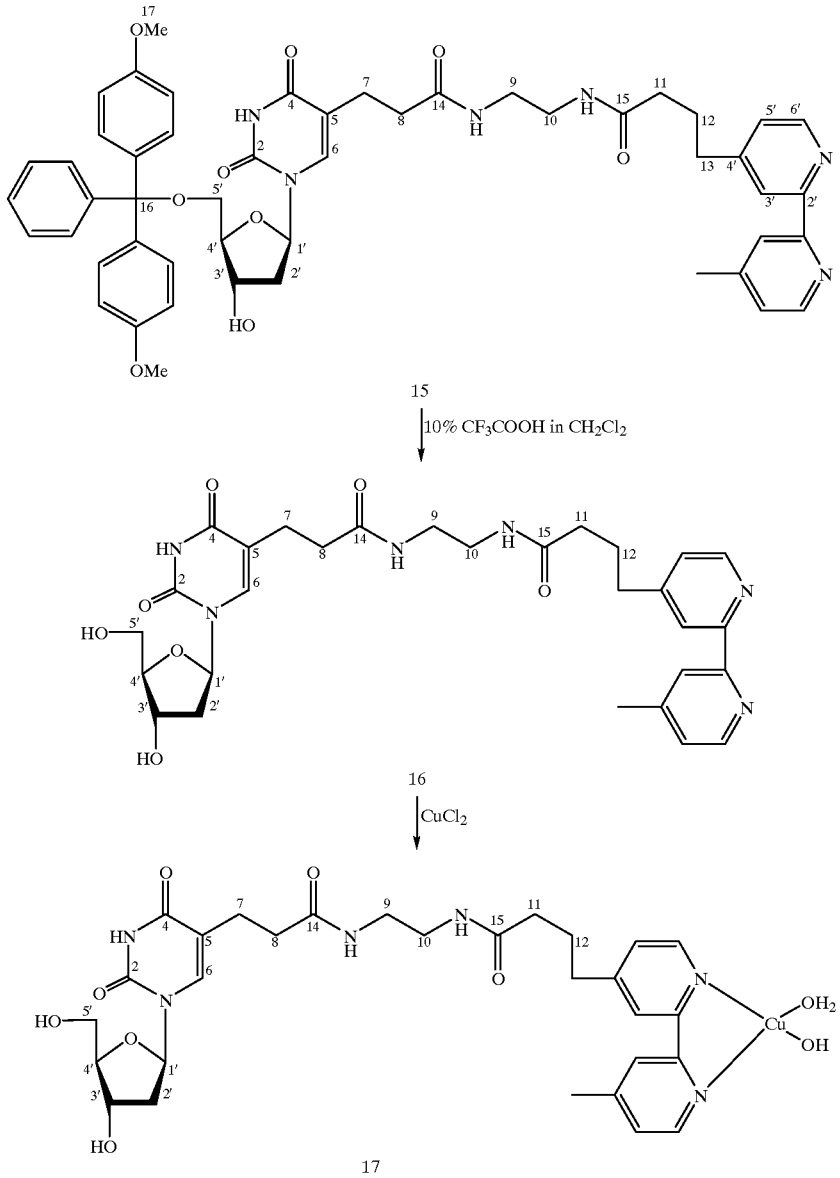
SCHEME 4A
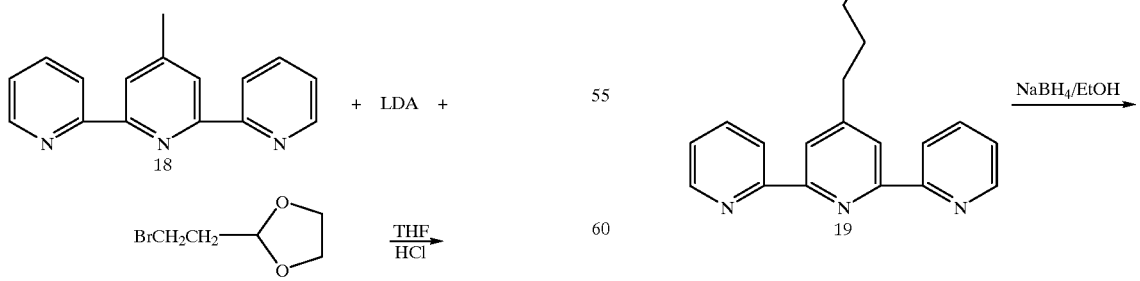

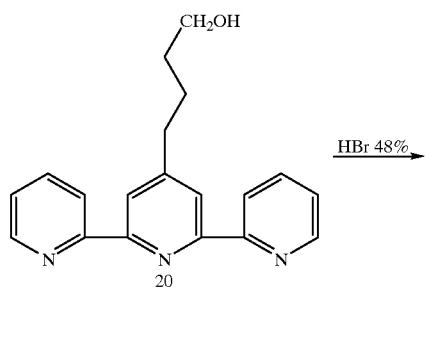
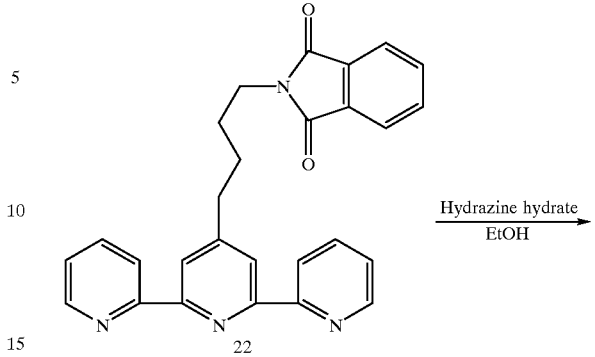
SCHEME 4B
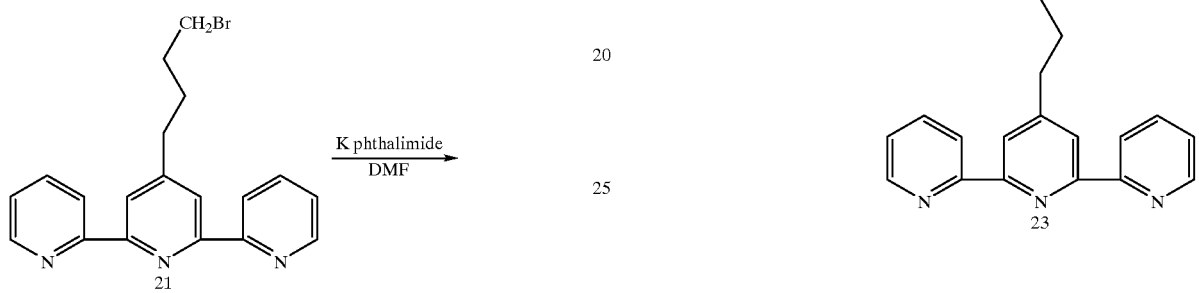
SCHEME 5
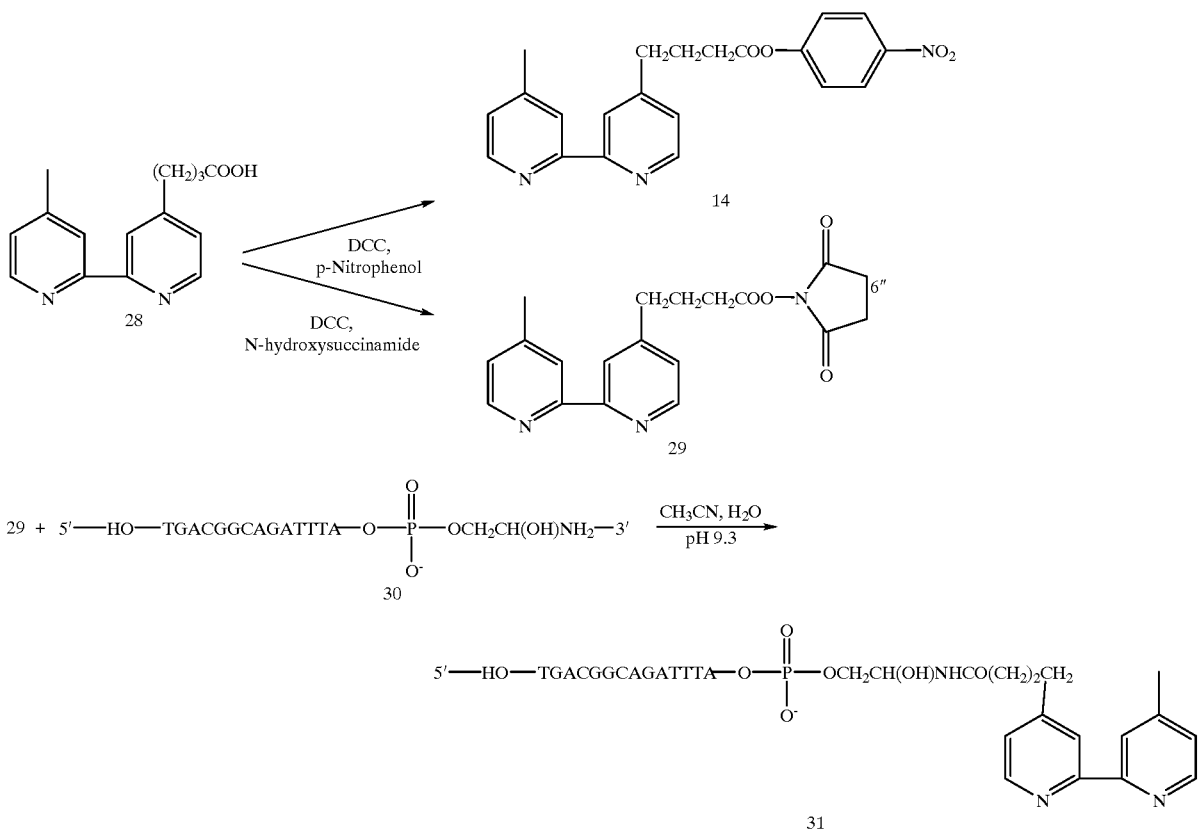

-continued

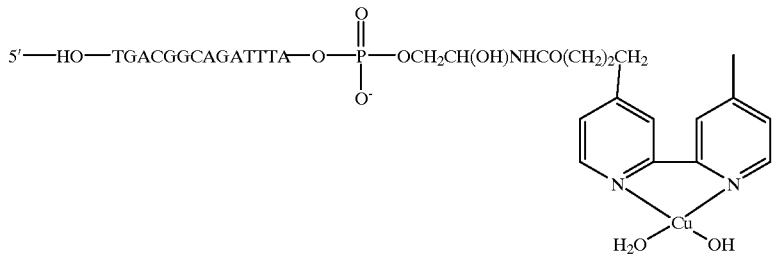

32

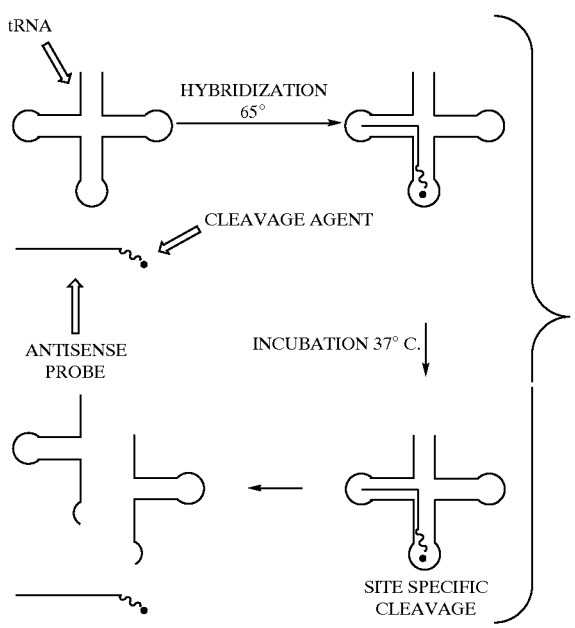

SCHEME 6

What we claim is:

1. A compound comprising a metal complex effective for hydrolyzing RNA, wherein said metal complex covalently linked at any location where chemical derivatization is possible to a nucleoside, nucleotide or oligodeoxynucleotide.

2. A compound of claim 1 which exhibits sequence-directed hydrolysis of RNA wherein said metal complex is linked to an oligodeoxynucleotide.

3. The compound of claim 1 wherein said metal complex is selected from the group of complexes formed by reacting 2,2':6',2''-terpyridine and copper(II); 2,2'-bipyridine and copper(II); 4,4'-dimethyl-2,2'-bipyridine and copper(II); 7-(N-methyl)-2,12-dimethyl-3,7,11,17-tetraazabicyclo[11.3.1]heptadeca-1 (17),2,11,13,15-pentaene and zinc(II); 2,12-dimethyl-3,7,11,17-tetraazabicyclo[11.3.1]heptadeca-1 (17),2,11,13,15-pentaene and zinc (II); and 2,10-dimethyl-3,6,9,12-tetraazabicyclo[9.3.1]pentadeca-1 (15)-2,10,12,15-pentaene and copper(II).

4. A compound of claim 1 wherein said metal complex is linked off the C-5 position of uracil in a 2'-deoxy-uridine nucleoside or nucleotide; the C-4 or C-5 position of cytosine in a 2'-deoxy-cytidine nucleoside or nucleotide; the N-6 position of adenine in a 2'-deoxy-adenosine nucleoside or nucleotide or the N-2 or O-6 position of guanine in a 2'-deoxy-guanosine nucleoside or nucleotide.

5. The compound of claim 4 wherein said metal complex is selected from the group of complexes formed by reacting 2,2':6',2''-terpyridine and copper(II); 2,2'-bipyridine and copper(II); 4,4'-dimethyl-2,2'-bipyridine and copper(II); 7-(N-methyl)-2,12-dimethyl-3,7,11,17-tetraazabicyclo[11.3.1]heptadeca-1 (17),2,11,13,15-pentaene and zinc(II); 2,12-dimethyl-3,7,11,17-tetraazabicyclo[11.3.1]heptadeca-1 (17),2,11,13,15-pentaene and zinc (II); and 2,10-dimethyl-3,6,9,12-tetraazabicyclo[9.3.1]pentadeca-1 (15)-2,10,12,15-pentaene and copper(II).

6. The compound of claim 1 wherein the metal in said metal complex is selected from the group consisting of copper, zinc and cobalt.

7. The compound of claim 1 wherein the ligand in said metal complex is selected from the group consisting of 2,2'-bipyridine and substituted 2,2'-bipyridines.

8. The compound of claim 1 wherein the ligand in said metal complex is selected from the group consisting of 2,2':6',2''-terpyridine and effective substituted 2,2':6',2''-terpyridines.

9. The method of covalently linking a metal complex effective for RNA hydrolysis to a nucleoside, nucleotide or oligodeoxynucleotide comprising reacting said nucleoside, nucleotide or oligodeoxynucleotide and metal complex under conditions to covalently link said metal complex to said nucleoside, nucleotide or oligodeoxynucleotide at any location where chemical derivatization is possible.

10. The method of claim 9 comprising reacting said nucleoside, nucleotide or oligodeoxynucleotide and an organic ligand, when complexed with a metal ion is effective in the hydrolysis of RNA, to covalently link said organic ligand to said nucleoside, nucleotide or oligodeoxynucleotide and, then, reacting the resulting compound with a metal ion effective in the hydrolysis of RNA to attach said metal ion to said organic ligand.

11. The method of claim 9 wherein said metal ion is first reacted with said ligand to form a complex which is then reacted with said nucleoside, nucleotide or oligodeoxynucleotide to covalently link said complex at any location where chemical derivatization is possible.

12. The compound which is a complex of 5-[3-[[2-[[4-[4'-methyl[2,2'-bipyridin]-4-yl]-1-oxobutyl]amino]ethyl]amino]-3-oxopropyl]-2'-deoxy-uridine and copper(II) of the formula

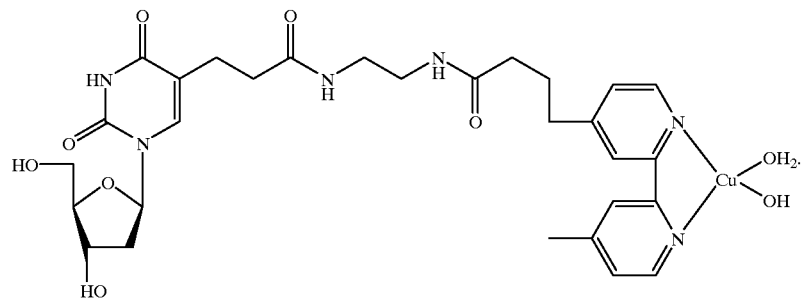
13. The compound which is a complex of 3'-[4-[4'-methyl (2,2'-bipyridin]-4-yl]butylphosphate]-2'2deoxythymidine ammonium salt and copper(II) of the formula
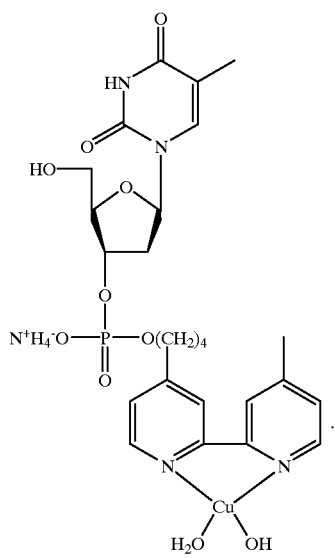
14. A compound which is a complex of 5'[4-[4'-methyl (2,2'-bipyridin]-4-yl]butylphosphate]-2'-deoxythymidine triethylammonium salt and copper(II) of the formula
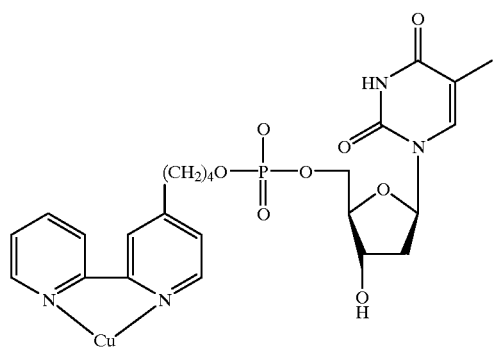
* * * * *